US006949692B2

(12) United States Patent
Dove et al.

(10) Patent No.: US 6,949,692 B2
(45) Date of Patent: Sep. 27, 2005

(54) METHOD FOR IDENTIFYING MUTANTS AND MOLECULES

(75) Inventors: William F. Dove, Madison, WI (US); Alexandra Shedlovsky, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/114,973

(22) Filed: Jul. 14, 1998

(65) Prior Publication Data

US 2002/0133831 A1 Sep. 19, 2002

Related U.S. Application Data

(63) Continuation of application No. 08/751,292, filed on Nov. 18, 1996, now Pat. No. 5,780,236.

(51) Int. Cl.[7] .................... G01N 33/00; A01K 67/00; A01K 67/027; C12N 15/00
(52) U.S. Cl. ................. 800/22; 800/3; 800/8; 800/9; 800/10; 800/21
(58) Field of Search ............................. 800/8, 9, 10, 3, 800/21, 22

(56) References Cited

U.S. PATENT DOCUMENTS

| 5,283,170 A | * | 2/1994 | Cassou et al. ................. 435/1 |
| 5,492,808 A | | 2/1996 | de la Chapelle et al. |
| 5,780,236 A | * | 7/1998 | Dove et al. ..................... 435/6 |

FOREIGN PATENT DOCUMENTS

WO WO 92/21229 12/1992

OTHER PUBLICATIONS

Bilger, A. et al. Manipulation of the Mouse Germline in the Study of Min–Induced Neoplasia. Seminars in Cancer Biology 7:249–260, 1996.*
Dietrich, W.F. et al. Genetic Identification of Mom–1, a Major Modifier Locus Affecting Min–Induced Intestinal Neoplasia in the Mouse. Cell 75:631–639, Nov. 1993.*
Moser, A.R. et al. A Dominant Mutation that Predisposes to Multiple Intestinal Neoplasia in the Mouse. Science 247:322–324, Jan. 1990.*
Shedlovsky, A. et al. Induction of Recessive Lethal Mutations in the T/t–H–2 Region of the Mouse Genome by a Point Mutagen. Genetical Research 47(2):135–142, Apr. 1986.*
Antoch, Marina P. et al., "Functional Identification of the Mouse Circadian Clock Gene by Transgenic BAC Rescue," *Cell* 89:655–667 (1997).
Balling, Rudi, "ENU–Mouse Mutagenesis Screen," (Application for Support of a Research Center).
Bateman, Nigel, "Sombre, A Viable Dominant Mutant in the House Mouse," *The Journal of Heredity* 186–189.

Bazin et al., "Genetic studies of phenotypic revertants of the vestigial mutant in *Drosophila melanogaster*, induced by bromouridine and ethyl methanesulfonate," *Mutation Research* 105:65–72 (1982).
Brown et al., "Mouse mutagenesis–systematic studies of mammalian gene function," *Human Molecular Genetics* 7:1627–1633 (1998).
Brunialti et al., "The Mouse Mutation Sarcosinemia (sar) Maps to Chromosome 2 in a Region Homologous to Human 9q33–q34," *Genomics* 36:182–184 (1996).
Church et al., "Isolation of genes from complex sources of mammalian gene using exon amplification," *Nat. Genet.* 6:98–105 (1994) abstract.
Cobb et al., "Biochemical and molecular analysis of spontaneous and induced mutations at the mouse Mod–1 locus," *Mutation Research* 234:1–7 (1990).
Collaborative Study Group for the Micronucleus Test, "Strain difference in the micronucleus test," *Mutation Research* 204:307–316 (1988).
Collaborative Study Group for the Micronucleus Test, "Single Virsus multiple dosing in the micronucleus test: the summary of the fourth collaborative study by CSGMT/JEMS.MMS," *Mutation Research* 234:205–222 (1990).
Cormier, et al., "Secretory phospholipase Pla2g2a confers resistance to intestinal tumorigenesis," *Nature Genetics* 17:88–91 (1997).
De Stasio, et al., "Characterization of Revertants of unc–93(e1500) in *Caenorhabditis elegans* Induced by N–ethyl–N–nitrosourea," *Genetics* 147–597–608 (1997).
Dickie, Margaret M., "Mutations at the Agouti Locus in the Mouse," *The Journal of Heredity,* 20–25.
Dickie, Margaret M., "A New Viable Yellow Mutation in the House Mouse," *The Journal of Heredity* 84–86.
Dove, William F., "Anecdotal, Historical and Critical Commentaries on Genetics, The Gene, the Polygene, and the Gemome" *Genetics* 134:999–1002 (1993).
Dove, William F., "Anecdotal, Historical and Critical Commentaries on Genetics, Transparent Vertebrates and Their Genetic Images" *Genetics* 137:339–341 (1994).
Ehling et al., "Induction of specific–locus mutations in female mice by 1–3thyl–1–nitrosourea and procarbazine," *Mutation Research* 202:139–146 (1988).

(Continued)

*Primary Examiner*—Joseph Woitach
(74) *Attorney, Agent, or Firm*—Quarles & Brady LLP (57) ABSTRACT

Methods for breeding mutagenized mice permit detection of genetic loci that in heterozygous mutated form can modify a known index phenotype involves crossing a mutagenized founder strain and a second strain of mice carrying an allele at a locus that confers the index phenotype. In the test generation, clusters of individuals are observed to deviate from the typical phenotype. The genetic material and molecules encoded thereby can be obtained using available methods. Improved and compact methods are also disclosed.

31 Claims, 1 Drawing Sheet

OTHER PUBLICATIONS

Ehling, U.H., "Germ–cell mutations in mice: Standards for protecting the human genome," *Mutation Research* 213:43–53 (1989).

Fahrig, Rudolf, "Similar pigmentation characteristics in the specific–locus and the mammalian spot test," *The Journal of Heredity* 76:421–426 (1985).

Favor, Jack, "Characterization of dominant cataract mutations in mice: penetrance, fertility and homozygous viability of mutations recovered after 250 mg/kg ethylnitrosourea paternal treatment," *Genet. Res., Camb.* 44:183–197 (1984).

Favor et al., "Towards an understanding of the nature and fitness of induced mutations in germ cells of mice: homozygous viability and heterozygous fitness effects of induced specific–locus, dominant cataract and enzyme–activity mutations," *Mutation Research* 212:67–75 (1989).

Favor et al., "The effect of dose fractionation on the frequency of ethylnitrosourea–induced dominant cataract and recessive specific locus mutations in germ cells of the mouse," *Mutation Research* 198:269–275 (1988).

Favor et al., "The frequency of dominant cataract and recessive specific–locus mutations and mutation mosaics in $F_1$ mice derived from post–spermatogonial treatment with ethylnitrosourea," *Mutation Research* 229:105–114 (1990).

Generoso et al., "Mutagen–induced fetal anomalies and death following treatment of females within hours after mating," *Mutation Research* 199:175–181 (1988).

Giometti et al., "Detection of Heritable Mutations as Quantitative Changes in Protein Expression," *The Journal of Biological Chemistry* 262:12764–12767 (1987).

Giometti et al., "A Heritable Variant of Mouse Liver Ornithine Aminotransferase (EC2.6.1.13) Induced by Ethylnitrosourea," *The Journal of Biological Chemistry* 263:15781–15784 (1988).

Giometti et al., "Heritable protein variants induced by exposure to ethylnitrosourea: Heritability, subcellular location, and tissue distribution," *Mutation Research* 202:9–17 (1988).

Gould et al., "Action of Min and Mom1 on Neoplasia in Ectopic Intestinal Grafts," *Cell Growth & Differentiation* 7:1361–1368 (1996).

Harte et al., "Genetic Analysis of Mutations at the Glued Locus and Interacting Loci in *Drosophila Melanogaster*," *D. Melanogaster G1 Mutations* 477–501 (1982).

Hayashi et al., "Difference between intraperitoneal and oral gavage application in the micronucleus test," *Mutation Research* 223:329–344 (1989).

Hitotsumachi et al., "Dose–repetition increases the mutagenic effectiveness of N–ethyl–N–nitrosourea in mouse spermatogonia," *Proc. Natl. Acad. Sci. USA* 82:6619–6621 (1985).

Holdener et al., "Phenotypic and physical analysis of a chemically induced mutation disrupting anterior axial development in the mouse," *Mammalian Genome* 6:474–475 (1995).

Holdener et al., "Physical Localization of eed: A Region of Mouse Chromosome 7 Required for Gastrulation," *Genetics* 24:447–456 (1995).

Huang et al., "Comparison of baseline sister–chromatid exchanges (SCE), cyclophosphamide–, ethylnitrosourea (ENU)–induced SCE, ENU–induced cell–cycle delay and chromosome aberrations between Peru and laboratory mice," *Mutations Research* 230:93–100 (1990).

Johnson et al., "Molecular Analysis of 36 Mutations at the Mouse pink–eyed dilution (p) Locus," *Genetics* 141:1563–1571 (1995).

Johnson et al., "High resolution metrical analysis applied to the assessment of damage associated with induced mutations in the mouse," *Mutation Research* 229:141–159 (1990).

Justice et al., "Induction of new mutations in a mouse t–haplotype using ethylnitrosourea mutagenesis," *Genet. Res., Camb.* 47:187–192 (1986).

Kenyon, Cynthia, "The Nematode *Caenorhabditis elegans*," *Science* 240:1448–1452 (1988).

Kerscher et al., "Two New Cataract Loci, Ccw and To3, and Further Mapping of the Npp and Opj Cataracts in the Mouse," *Genomics* 36:17–21 (1996).

King et al., "The Mouse Clock Mutation Behaves as an Antimorph and Maps Within the $W^{19H}$ Deletion, Distal of Kit," *Genetics* 146:1049–1060 (1997).

Klopp et al., "Three Murine Cataract Mutants (Cat2) Are Defective in Different γ–Crystallin Genes," *Gemonics* 52:152–158 (1998).

Kratochvilova et al., "Dominant cataract and recessive specific–locus mutations detected in offspring of procarbazine–treated male mice," *Mutation Research* 88:298–301.

Lewis et al., "ENU mutagenesis in the mouse electrophoretic specific–locus test, 1. Dose–response relationship of electrophoretically–detected mutations arising from mouse spermatogonia treated with ethylnitrosourea," *Mutation Research* 249:311–315 (1991).

Lewis et al., "ENU mutagenesis in the mouse electrophoretic specific–locus test 2. Mutational studies of mature oocytes," *Mutation Research* 296:129–133 (1992).

Martelli et al., "Comparison of micronucleus formation in mouse bone marrow and spleen," *Mutation Research* 292:63–67 (1993).

McDonald, J. David, "Using High–Efficiency Mouse Germline Mutagenesis to Investigate Complex Biological Phenomena: Genetic Diseases, Behavior, and Development," *High–Efficiency Mouse Germline Mutagenesis* 303–305 (1995).

McDonald et al., "Hyperphenylalaninemia in the hph–1 Mouse Mutant," *Pediatric Research* 23:63–67 (1987).

McDonald et al., "Biochemical Defect of the hph–1 Mouse Mutant Is a Deficiency in GTP–Cyclohydrolase Activity," *Journal of Neurochemistry* 50:655–657 (1987).

Miller et al., "Genetic Studies of the Mouse Mutations mahogany and mahoganoid," *Genetics* 146:1407–1415 (1997).

Montagutelli et al., "aku, a Mutation of the Mouse Homologous to Human Alkaptonuria, maps to Chromosome 16," *Genomics* 19:9–11 (1994).

Moore et al., "The Murine Dilute Suppressor Gene dsu Suppresses the Coat–Color Phenotype of Three Pigment Mutations That Alter Melanocyte Morphology, d, ash and In," *Genetics* 119:933–941 (1988).

Morris, Suzanne M., "The genetic toxicology of 5–fluoropyrimidines and 5–chlorouracil," *Mutation Research* 297:39–51 (1993).

Preat, Thomas, "Characterization of Suppressor of fused, a Complete Suppressor of the fused Segment Polarity Gene of *Drosophila melanogaster*," *Genetics* 132:725–736 (1992).

Provost et al., "Response to the Commentary Article: Comparison of mutation frequencies obtained using transgenes and the specific–locus mutation system in male mouse–germ cells," *Mutation Research* 298:145–147 (1992).

Provost et al., "Transgenic systems for in vivo mutation analysis," *Mutation Research* 288:133–149 (1993).

Rinchik et al., "A strategy for fine–structure functional analysis of a 6– to 11–centimorgan region of mouse chromosome 7 by high-efficiency mutagenesis," *Proc. Natl. Acad. Sci. USA* 87:896–900 (1990).

Rinchik, Eugene M., "Chemical mutagenesis and fine–structure functional analysis of the mouse genome," *TIG* 7:15–21 (1991).

Rinchik et al., "Deletion Mapping of Four Loci Defined by N–Ethyl–N–Nitrosourea–Induced Postimplantation–lethal Mutations Within the pid–Hbb Region of Mouse Chromosome 7," *Genetics* 135:1117–1123 (1993).

Rinchik et al., "Molecular Analysis of Radiation–induced albino (c)–Locus Mutations That Cause Death at Preimplantation Stages of Development," *Genetics* 135:1107–1116 (1993).

Rinchik et al., "Molecular Genetics of the Brown (b)–Locus Region of Mouse Chromosome 4. I. Origin and Molecular Mapping of Radiation– and Chemical–Induced Lethal Brown Deletions," *Genetics* 137:845–854 (1994).

Ranchik, Eugene M., "Molecular Genetics of the Brown (b)–Locus Region of Mouse Chromosome 4. II. Complementation Analyses of Lethal Brown Deletions," *Genetics* 137:855–856 (1994).

Rubin, Gerald M., "*Drosophila melanogaster* as an Experimental Organism," *Science* 24:1453–1459 (1988).

Ruddle et al., "Hybrid Cells and Human Genes," *Genetic Analysis* 122–157 (1974).

Russell et al., "The Mouse Specific–Locus Test with Agents Other Than Radiations, Interpretation of Data and Recommendations for Further Work," *Mutation Research* 86:329–354 (1981).

Russell et al., "The paternal genome in mouse zygotes is less sensitive to ENU mutagenesis than the maternal genome," *Mutation Research* 248:203–209 (1991).

Russell et al., "Frequency and nature of specific–locus mutations induced in female mice by radiations and chemicals: a review," *Mutation Research* 296:107–127 (1992).

Russell et al., "Structural differences between specific–locus mutations induced by different exposure regimes in mouse spermatogonial stem cells," *Mutation Research* 288:187–195 (1993).

Russell et al., "Dose–response curve for ethylnitrosourea–induced specific–locus mutations in mouse spermatogonia," *Proc. Natl. Acad. Sci. USA* 79:3589–3591 (1982).

Sandulache et al., "Genetic Instability at the agouti Locus of the Mouse (*Mus musculus*). I. Increased Reverse Mutation Frequency to the $A^W$ Allele in A/a Heterozygotes," *Genetics* 137:1079–1087 (1994).

Searle et al., "Mouse homologues of human hereditary disease," *J. Med. Genet.* 31:1–19 (1994).

Shedlovsky et al., "Saturation germ line mutagenesis of the murine t region including a lethal allele at the quaking locus," *Proc. Natl. Acad. Sci. USA* 85:180–184 (1988).

Shedlovsky et al., "Mouse Models of Human Phenylketonuria," *Genetics* 134:1205–1210 (1993).

Shoemaker et al., "Studies of neoplasia in the Min mouse," *Biochimica et Biophysica Acta* 1332:F25–F48 (1997).

Simon et al., "Ras1 and a Putative Guanine Nucleotide Exchange Factor Perform Crucial Steps in Signaling by the Sevenless Protein Tyrosine Kinase," *Cell* 67:701–716 (1991).

Suzuki et al., "The concomitant detection of gene mutation and micronucleus induction by mitomycin C in vivo using lacZ transgenic mice," *Mutation Research* 285:219–224 (1993).

Takahashi et al., "Forward and Reverse Genetic Approaches to Behavior in the Mouse," *Science* 264:1724–1732 (1994).

van Zeeland et al., "DNA adduct formation in mouse testis by ethylating agents: a comparison with germ–cell mutagenesis," *Mutation Research* 231:55–62 (1990).

Vitaterna et al., "Mutagenesis and Mapping of a Mouse Gene, Clock, Essential for Circadian Behavior," *Science* 264:719–725 (1994).

Wang et al., "Coat Color Genetics of Peromyscus: II. Tan Streak—A New recessive Mutation in the Deer Mouse, *P. maniculatis,*" *The Journal of Heredity* 84: 305–307 (1993).

Yamamoto et al., "Dose–dependent Induction of Both Pepsinogen–altered Pyloric Glands and Adenocarcinomas in the glandular Stomach of C3H Mice Treated with N–Methyl–N-–nitrosourea," *J. Cancer Res.* 88:238–244 (1997).

Yamasaki et al., "Mutational activation of H–ras oncogene transformability by alkylnitrosourea–induced DNA damage," *Mutation Research* 266:241–252 (1992).

Hully et al., "Transgenic Hepatocarcinogenesis in the Rat," *American Journal of Pathology* 145:384–397 (1994).

Gould et al., "Genetic Evaluation of Candidate Genes for the Mom1 Modifier of Intestinal Neoplasia in Mice," *Genetics* 144:1777–1785 (1996).

King et al., "Positional Cloning of the Mouse Circadian Clock Gene", *Cell* 89:641–653 (1997).

Kusumi et al., "The Mouse Pudgy Mutation Disrupts Delta Homologue DII3 and Initiation of Early Somite Boundries", *Nature Genetics* 19:274–278 (1998).

Moser et al., A Dominant Mutation That Predisposes to Multiple Intestinal Neoplasia in the Mouse:, *Science* 247:322–324 (1990).

Moser et al., "The Min (Multiple Intestinal Neoplasia) Mutation: Its Effect on Gut Epithelial Cell Differentiation and Interaction with a Modifier System", *The Journal of Cell Biology* 116:6, 1517–1526 (1992).

Dietrich et al., "Genetic Identification of Mom–1, a Major Modifier Locus Affecting Min–Induced Intestinal Neoplasia in the Mouse", *Cell* 75:631–639 (1993).

Friedrich, "Moving beyond the genome projects", *Nature Biotechnology* 14:1234–1237 (1996).

Roush, "Biotech Finds a Growth Industry", *Science* 273:300–301 (1996).

Zhang et al., "Positional cloning of the mouse obese gene and its human homologue", *Nature* 372:425–432 (1994).

Shedlovsky et al., "Induction of recessive lethal mutations in the T/t–H–2 region of the mouse genome by a point mutagen", *Genet Res., Camb* 47:135–142 (1986).

* cited by examiner

FIG 1

METHOD FOR IDENTIFYING MUTANTS AND MOLECULES

CROSS-REFERENCE TO RELATED APPLICATIONS

This application is a continuation-in-part of application Ser. No. 08/751,292 filed Nov. 18, 1996, now U.S. Pat. No. 5,780,236, incorporated herein in its entirety by reference.

STATEMENT REGARDING FEDERALLY SPONSORED RESEARCH OR DEVELOPMENT

This invention was made with United States government support awarded by the following agency: NIH Grant Nos: CA23076, CA50585, CA63677, and CA 07175. The United States has certain rights in this invention.

BACKGROUND OF THE INVENTION

Worldwide efforts to determine the genomic DNA sequences of humans and other animals are ongoing. Such efforts typically focus on obtaining sequence information from cDNAs in libraries created from RNAs of various tissues. Thus, collections of "expressed sequence tags" (ESTs) include portions of coding regions from most human genes.

Although ESTs provide useful structural information, they offer little insight into the functional relationship among genes. The functional relationship is of particular importance to determining the set of genes involved in a biological process and, subsequently, to developing pharmaceutical agents that affect one or more of the components of the biological process. See, e.g., Friedrich, G. A., "Moving Beyond the Genome Projects: Does the Future of Genomics-Based Drug Discovery Lie With the Mouse?," *Nature Biotechnology* 14:1234–1237 (1996).

Friedrich argues in favor of using model systems that mirror human physiology in determining which genes may be involved in a biological process, and suggests that the mouse is an excellent model organism for human biology in that it shares with humans most salient aspects of mammalian physiology. The genomes of mice and humans are approximately the same in size, organization, and structure. Friedrich proposes that the mouse can be developed as an effective tool for drug development. Friedrich puts forth a "radical" suggestion that there is no logical barrier hindering large-scale phenotypic screens using mice.

Friedrich proposes using an insertional mutagen in embryonic stem cells to generate random mutations in the mouse genome, then screening for a variety of predetermined phenotypes and cloning affected genes.

In particular, the physiology of, and treatments for, colon cancer are of particular biomedical interest. Colon cancer is one of the most prevalent malignancies in the Western world, with an estimated 145,000 new cases and 60,000 deaths each year in the United States alone. Genetic factors play a key role in this disease. Mutations in the human adenomatous polyposis coli (APC) gene cause a set of familial colon cancer syndromes. Mice carrying a mutation in a corresponding gene (Apc) also develop many intestinal adenomas. Heterozygotes for the Min (Multiple Intestinal Neoplasia) allele of the mouse Apc gene develop numerous intestinal and colonic adenomas [on average 29 Å 10, on a C57BL/6J (or equivalent derivative) background] that are similar in morphology to the adenomas seen in human inherited colonic polyposis syndromes such as familial adenomatous polyposis and Gardner's syndrome. Min/Min homozygotes die in utero. The Min mutation maps to mouse chromosome 18. The sequence of the Apc gene is known and published. Min mice carry a nonsense mutation in exon 15 of the mouse Apc gene (a mutation of the sort typically seen in human colon cancer kindreds). Mice carrying Min thus provide a model system for studying human familial adenomatous polyposis.

A locus (Mom-1) that strongly modifies the tumor number in heterozygous Min/+ mice was mapped to distal chromosome 4. Dietrich, W. F., et al., "Genetic Identification of Mom-1, a major modifier locus affecting Min-induced intestinal neoplasia in the mouse," *Cell* 75:631–639 (1993). Mom-1 lies in a region of synteny conservation with human chromosome 1p35-36, a region of frequent somatic loss of heterozygosity in a variety of human tumors, including colon tumors. Mom-1 is only one of an unknown number of Loci that modify the expression of an inherited cancer syndrome, and it does not explain all of the genetic variation in tumor number in intraspecific backcrosses.

What is lacking is a systematic method for pinpointing genetic loci involved in modifying known phenotypes, by enhancing or suppressing. In the particular case of colon cancer in humans and animals, it would be desirable to locate the sequences in the genome (and the molecules encoded by those sequences) that are involved in the appearance of intestinal adenomas. The lack of such a systematic method has limited understanding of oncogenesis and, as such, has precluded development of pharmaceuticals that modify the oncogenic process. A systematic method should include not only non-essential loci, for which numerous mutant alleles can be found among homozygous inbred mouse strains, but also essential loci, for which mutant alleles in heterozygous form may influence the phenotype. Mutations that inactivate an essential gene will normally be lethal when homozygous, and so will not be found among inbred mouse strains.

BRIEF SUMMARY OF THE INVENTION

The present invention permits detection of a genetic locus or loci that can modify a chosen known phenotype conferred by a chosen dominant allele. The method includes a mutagenic process that facilitates identifying and isolating the genetic sequences that encode the molecules that can modify the chosen phenotype, as well as the phenotype-modifying molecules themselves.

The method can be practiced using inbred strains of non-human animals, which are preferably mammals, and more preferably rodents. Inbred strains of mice, rats and rabbits are available. In the present method, mice are the non-human mammalian animals of choice, because of the synteny between humans and mice and because the genetics and breeding of mice are highly developed. Further, the mouse can exhibit disease phenotypes that are very similar to those of humans, as in the exemplified embodiment. The murine genetic sequences and the molecules obtained in the method are used to secure corresponding sequences and molecules from humans. The human sequences and molecules are then employed in known methods to develop pharmaceutical agents.

The basic breeding method includes the following steps. Each of a set of mice of a founder inbred mouse strain is mutagenized and then bred to the same inbred strain to produce an inbred holding generation ("Generation 1" or "Gen1"). The animals of the Gen1 founder mouse strain carry random point mutations relative to wild-type mice of that strain. Gen1 mice are outcrossed with a mouse of an index inbred mouse strain to obtain Gen1F$_1$ progeny. The index inbred mouse strain carries a dominant allele at a locus known to confer a chosen phenotype. The chosen phenotype is designated the "index phenotype." The index phenotype, which focuses the screening method on the phenotype of interest, is characterized in an index strain and provides a reference phenotype against which possible mutants can be compared. The dominant index allele can include any condition that brings a biological process into a range in which it responds to heterozygous enhancer or suppressor mutations of the sort identified in the present invention. The condition can be a cognizable genetic condition or might even be a non-genetic environmental condition. At least some of the Gen1 F$_1$ progeny carry both the dominant allele and at least one random mutation that may modify the index phenotype conferred by the dominant allele. A founder animal is judged to be of interest if a subset of its Gen1F$_1$ progeny are extensively modified for the index phenotype.

When a founder mouse has at least one Gen1F$_1$ offspring that displays a modified phenotype relative to control animals, the founder (Gen1) animal is crossed to an unmutagenized mouse of the founder strain to produce second generation (Gen2) offspring. Those offspring are again outcrossed to the index strain to obtain Gen2F$_1$ progeny. The presence of a phenotype-modifying mutation is then verified if a subset of the Gen2F$_1$ progeny are also modified for the index phenotype. Again, a cluster of animals with modified index phenotypes gives increasing confidence that the Gen1 founder carries a mutation of interest.

Genetic material that comprises the phenotype-modifying mutation can then be obtained using methods known to the art. Molecules encoded by the genetic material may also be obtained. The obtained genetic materials and molecules (or corresponding human equivalents) are used in methods known to the art to produce pharmaceutical agents that can ameliorate phenotypes noted in human or non-human patients affected in the biological process of interest.

It is an object of the present invention to provide a rapid, focused approach to obtaining genes in a model mammalian organism that can affect a biomedically-relevant phenotype.

It is an advantage of the present invention that the method can simultaneously identify an ensemble of several genes that can modify the index phenotype.

It is another advantage of the present invention that the method can uncover genes having no other known phenotype.

The present invention offers advantages over existing methods of obtaining genes, such as analysis of ESTs, in that genes secured in the present method are necessarily relevant to a biological phenotype. In contrast, genome-sequencing methods can provide voluminous sequence information for many genes, but offer little or no guidance as to the functional relationship among sequenced genes.

BRIEF DESCRIPTION OF THE SEVERAL VIEWS OF THE DRAWINGS

FIG. 1 also depicts the survival times of individuals of four kindreds that exhibited progeny with longer or shorter survival times relative to the average survival time of Gen1F$_1$ mice carrying the index Min allele. Longer-surviving suppressor (Su) candidate kindreds 248 and 258 are shown as squares. Shorter-surviving enhancer (En) candidate kindreds 333 and 425 are shown as circles.

DETAILED DESCRIPTION OF THE INVENTION

A goal of the present invention is to identify genetic loci and genetic sequences that can modify a known phenotype. Although such analysis employing mutagenesis cannot be performed in humans for ethical reasons, the synteny and sequence conservation between human and mouse genomes provides a facile bridge to identify such loci and sequences in the human. It is likely that such sequences will correlate with existing human genetic sequence information. Thus, equivalent loci and genetic sequences can be sought in the human genome using conventional, available hybridization and PCR techniques.

The method is an index-directed, Cluster-enhanced, Modifier locus and Molecule identification method that can be referred to as an "ICMM method."

The availability of inbred mice having a well defined genetic composition and well-studied phenotypes that model human syndromes, diseases, and other conditions, makes the mouse the preferred mammalian species in which to practice the present method. A preferred mouse species is *Mus musculus*.

The breeding system described herein is premised upon the existence of a phenotype that is evident in mice heterozygous for the allele that confers the chosen index phenotype. It is always preferable to employ an index strain that carries an allele that gives the index phenotype in the heterozygous state. The index phenotype can be made "evident" by visual, biochemical, or other detection means. The phenotype-controlling allele can be lethal when present in the homozygous state. For cancer, the phenotype can relate either to effects that follow from the presence of an activated cancer-inducing allele or else from inactivation of a tumor suppressor gene that causes tumor formation in the absence of one normal copy of the gene. The phenotype can be governed by an allele on a sex chromosome or on an autosome. If the allele is on a sex chromosome, the breedings described herein are modified in a manner known to the art to ensure that the allele is maintained in the breeding pool.

The index phenotype is preferably conferred by a single dominant allele, although by taking care to produce suitable founder animals, phenotypes under the control of more than one locus can be studied in the method. It is not necessary that the phenotype-conferring allele is a defined genetic sequence, but rather the allele can be defined by classical genetic methods. It is advantageous that the allele is tightly linked to a genetic marker for genotype analysis, as is described elsewhere herein. With the dense microsatellite map of the mouse genome currently available, this condition is always met.

Phenotype-modifying loci are obtained in the present invention. A "modification" is any demonstrable change in an index phenotype relative to control animals lacking the phenotype-modifying allele, including, without limitation, enhancing or suppressing a phenotype, such as prolonging or shortening an animal's life span or circadian behavior. It is not necessary that the whole animal be affected by the modification. For example, a modified phenotype may be a change in a particular behavior or a change in the level of a particular biomolecule, such as a blood protein, after introducing a phenotype-modifying mutant allele in the method of the present invention. The assay for modified outliers in the first stage of the screen, Gen1F$_1$, will usually be relatively crude. One must judge whether an outlier is in the first or last 10 percentile range of the phenotypic distribution. For example, in a strain of mice having a well-defined running activity governed by a single dominant mutation (Clock)," the method described herein can be used to obtain animals having modified timing of that running activity. The genetic material (and protein molecules) responsible for that modification can be obtained by mapping and positionally cloning the modifying mutation.

The system is particularly amenable to study of genetic interactions in cancers known to have a genetic component. In particular, humans that carry an aberrant APC gene are predisposed to develop numerous tumors in the intestinal tract. Mice heterozygous for the Min allele of Apc, the murine homolog of human APC, also develop numerous tumors in the intestinal tract, similar to human inherited colonic polyposis syndromes. It is demonstrated herein that mutations induced in the genome elsewhere than at the Apc locus can modify the survival rate and intestinal tumor load of mice carrying the Min allele at that locus.

Several important breeding considerations direct the selection of inbred mouse strains for use in the method. It is understood that those skilled in the art of mouse breeding are familiar with the breeding requirements of available mouse strains and such requirements need not be restated here.

The strain into which random mutations are introduced must be an inbred strain so that all modifications are the result of induced mutagenesis rather than genomic divergence. The strain should be susceptible to efficient germline mutagenesis. By "susceptible" the applicants intend that the strain have characteristic forward mutation rates of at least $1/500$ per gamete per locus. In addition, the strain should have a long breeding span of at least one year. Also, it is preferred that the strain yield large litters, on average 8 or more pups per litter. A strain meeting these requirements is the inbred strain BTBR, which is available from the Jackson Laboratory, Bar Harbor, Me.

It is important that the inbred strain in which mutations are induced can be distinguished from the strain that contains the phenotype-conferring allele, e.g., by restriction fragment length polymorphisms (RFLP) or by simple sequence length polymorphisms (SSLP). A high incidence of informative differences in standard genetic markers between the two strains is important for mapping and cloning any mutation of interest. In one embodiment of the invention, the index phenotype (Min) was provided on a background of C57BL/6J (or equivalent derivative) (hereinafter, "B6-Min"). An "equivalent derivative" has an index phenotype comparable to that of B6-Min on a genuine C57BL/6J background. The BTBR strain used for mutagenesis in this embodiment is polymorphic at approximately half of the SSLP marker loci, relative to the B6 inbred strain In heterozygous form, BTBR has no strong effect on the Min phenotype.

It is also important that the two strains used in the method be relatively free of polymorphic dominant modifiers of the chosen index phenotype. By "relatively free" the applicants intend that differences in the index phenotype between Gen1$F_1$ animals and the index strain be sufficiently minor so as not to mask the effects of newly induced mutations. One skilled in the art will be able to determine the permissible variation for any given index phenotype. For example, in the case of the Min index phenotype, Gen1$F_1$ animals should show no more than about a 1.5-fold change in tumor multiplicity compared to B6-Min. In the Clock case, there should be no more than a 30 minute shift in circadian rhythm.

In the method, the strain that is to be mutagenized is treated with a mutagenic agent that induces mutations in the germline. It is important, for reasons associated with subsequent detection and isolation of mutants of interest, that the mutagen be an efficient point mutagen that can induce at least one mutation per locus per 500 gametes in the founder animal strain. Ethylnitrosourea (ENU) is a suitable and preferred mutagen which introduces almost exclusively point mutations in the mouse germline. A suitable protocol for ENU mutagenesis of mice is described in Shedlovsky et al., *Genet. Res., Camb.* 47:135–142 (1986), incorporated herein by reference. It is preferred, but not essential, that the mutagenesis be performed on male mice, since it is possible to obtain many offspring from a single mutagenized male. The mice are then crossed with unmutagenized mice of the same strain to produce isogenic animals, heterozygous only for the various mutations induced by the mutagenesis.

Each member of the set of Gen1 animals is crossed to mice heterozygous for the mutation conferring the index phenotype. It is desirable to produce up to 1000 of such Gen1 animals, to maximize the statistical likelihood that each of the approximately $1 \times 10^5$ genes in the mouse genome is examined at least once. If the mutation frequency is 1 per locus per 500 gametes, a 1000-member library of Gen1 animals would contain an average of 2 hits for each locus that can modify the index phenotype. The probability that a salient locus would escape attention would then be $e^{-2}$ or $\tilde{e}10\%$. The cross can be done using Gen1animals of either gender, unless the index phenotype compromises the successful breeding of one gender. It is sometimes possible to foster offspring when the female parent is compromised.

The kindreds are evaluated as follows. The phenotypic behaviors of the full set of Gen1$F_1$ animals are scored as are the phenotypes of individual kindreds. Where no modification is present, the behavior of individuals in the kindred would range over the average behavior of the full set. However, if a modifying mutation has been induced, and since the founder parent was heterozygous for the modifying mutation, on average 50% of the members of the kindred will show an outlying phenotype.

To improve the statistical likelihood that a modified phenotype is genuine, it is preferred that the modification be observed in two or more animals of a kindred having four or more members. A further condensation of the method is possible under these conditions. See, infra. It is most preferred that the kindred have at least six members and that three or more members are affected. It may be fruitful, however, to study smaller kindreds containing a single extreme outlier.

The female parents of kindreds that evidence possible modification by the above-noted standard are then crossed to unmutagenized mice of the same founder strain to maintain the mutation on a fixed background (a "copying generation"). The offspring of the copying generation are crossed again to mice heterozygous for the chosen phenotype to assess whether any of their offspring carry a bona fide modifying mutation. A genotypic analysis can be performed to determine which of these offspring carry the gene that confers the index phenotype. It can be particularly important to characterize the offspring quickly if the phenotype is one that affects the lifespan of the Gen1 founder animals.

Mice shown by genotypic analysis to carry the index determinant are assessed as early as possible to determine whether any modification is apparent. If such a modified phenotype is observed, the specific genetic sequences responsible for the modification can be systematically identified using technology now available to the art. See, e.g., Zhang, Y. et al, "Positional cloning of the mouse obese gene and its human homologue," *Nature* 372:425–432 (1994); Kusumi, K. et al., "The mouse pudgy mutation disrupts Delta homologue D113 and initiation of early somite boundaries," *Nature Genetics*, 19:274 (1998); and King, D. P., et al., "Positional Cloning in the Mouse Circadian Clock Gene," *Cell* 89:641 (1997), all incorporated herein by reference in their entirety. Each gives a concrete example of mutation-guided positional cloning. In the latter example, mutations were induced with ENU. In this approach, murine coding sequences are identified on a contig (a contiguous nucleic sequence of a portion of a chromosome determined by analyzing of a set of overlapping component nucleic acid sequences) constructed in the region of markers linked to a mutation. The murine coding sequences were identified by exon trapping (Church, D. M., et al, *Nature Genet.* 6:98–105 (1994), incorporated herein by reference), sequencing of trapped exons, comparing the sequences of trapped exons to all sequences in Genbank, screening putative exons for the presence of corresponding RNA in a variety of tissues by northern blots and reverse-transcription PCR. Then, by known methods of hybridization to human genetic material, the corresponding human gene was obtained. Alternatively, PCR primers prepared from the murine genetic sequences can be used to amplify corresponding human sequences from human genetic material. One skilled in the art can readily determine the similarity required between marine-derived primers and human target sequences in PCR methods.

While the method described above is effective for finding segregating mutations that modify an index phenotype, the method is improved by providing a first improved method that more rapidly identifies modifiers having a severe and pronounced heterozygous enhancing or suppressing impact on an index phenotype, or by providing a second improved method that facilitates identifying and mapping modifiers by reducing genetic background noise. The improved methods are described below.

It is also noted that male gametes can now be advantageously harvested at sexual maturity (approximately 6 weeks for mice) and preserved indefinitely or used in an in vitro fertilization method, for example, according to the published method of Sztein, J. M., J. S. Farley J. S., A. F. Young and L. E. Mobraaten, "Motility of cryopreserved mouse spermatozoa affected by temperature of collection and rate of thawing," Cryobiology 35 (1):46–52 (1998), incorporated herein by reference in its entirety. By using the cryopreservation method, germplasm found to comprise a modifying mutation can be rescued and used in any cross described herein, even if the source animal is, at the time, too old or too ill to breed. Each male yields sufficient sperm to produce at least 500 progeny. In each cross described, it is also preferred that animals (or, more broadly, gametes) that potentially contribute a modifier into the cross be male animals (or gametes), unless a maternal effect is involved in the index phenotype, because so many more gametes can be screened using males rather than females. Depending upon the strains used, foster mothering may be required.

The first improved method, which is more compact and more efficient than the prior method, requires fewer crossing steps, eliminates a holding generation, and can be useful where the modified index phenotype accelerates death or reduces breeding capacity. This improved method sacrifices some of the strength of the 2-generation dominant modifier screen in that it does not present a candidate on the basis of a cluster of outliers on the survival curve and in that it loses strict isogenicity after the first generation. However, it does aim efficiently at modifiers in vital genes whose cloning can be pursued as described. In this improved method, one can detect new modifier alleles, both for extreme enhancer and suppressor outliers in the $F_1$ generation, or instead can use the cluster principle of the basic method to confirm subtle $F_1$ outliers by screening for clusters of animals more subtly modified in the backcross (N2) generation. An "extreme" outlying phenotype can be defined on a case-by-case basis, depending upon the nature of the index phenotype. A non-limiting example would be a phenotype enhanced or suppressed to a level below the tenth percentile or above the ninetieth percentile, respectively. In another case, for example, "extreme" levels might be established at the second and ninety-eighth percentiles. A "subtle" change is a change that is within statistical noise in the $F_1$ animals, but first becomes statistically significant in the backcross generation or subsequent cross.

In the first improved method, a mutagenized inbred animal of an appropriate strain is mated directly to an animal of the index strain to produce $F_1$ progeny that are screened for modified index phenotype.

If an $F_1$ animal appears to carry a modifier mutation, it is backcrossed to the index strain (with or without the index allele) to yield N2 progeny. At this generation, multiple animals are screened to find clusters of progeny with a modified phenotype. Clusters of animals that exhibit the modified phenotype carry the modifier mutation, while those that do not exhibit the modification fail to carry the mutation. Carriers must be heterozygous for alleles genetically linked to the locus, while non-carriers must be homozygous for the index strain at those same loci. Thus, these animals provide the material for mapping the new mutation using well-known PCR-based mapping methods (SSLPs and SNPs). Single nucleotide polymorphisms are described in Kruglyak, L. "The Use of a Genetic Map of Biallelic Markers in Linkage Studies," Nature Genetics 17:21 (1997), incorporated herein by reference in its entirety.

The second improved method facilitates identifying and mapping of modifying mutations by reducing genetic background noise. The method is an isogenic modifier screening method in which animals that contribute the dominant allele and the founder inbred animals that carry random point mutations share an inbred genetic background. Apart from the dominant index allele, the index animals are closely matched to the mutation-carrying founder inbred animals.

Two embodiments of this second improved method are contemplated. In the first embodiment, enhancer and suppressor modifiers can both be detected when the genetic background shared by the index animals and the founder animals has no apparent effect on the index phenotype. In an example of this embodiment, an index mouse strain can contain a Min allele at an Apc locus on a C57BL/6J (B6) background while the mutagenized founder animals can be B6 mice.

In the second embodiment of this method, the genetic background affects the index phenotype, in that when the dominant allele that confers the index phenotype is provided on a particular genetic background, the index phenotype is enhanced or suppressed in the animal, facilitating selective detection of suppressing or enhancing modifiers, respectively. The index strain can be a congenic derivative of a strain that has a genetic background that enhances or suppresses the index phenotype, wherein the congenic strain carries the dominant allele that confers an index phenotype. For example, in a congenic strain having a Min allele at an Apc locus, on the genetic background of the inbred BTBR strain, the Min phenotype is significantly enhanced.

Congenic inbred animals carrying the index allele are crossed to animals that have been mutagenized as described elsewhere herein to produce Gen1 animals. Suppression and/or enhancement of the index phenotype can be assessed as described. Where the index parent in this cross has an enhanced index phenotype, putative suppressing modifiers of the index phenotype can be apparent in some Gen1 animals as a shift in the index phenotype away from the enhanced level and toward the wild-type level. Putative modifiers in Gen1 animals can be mapped by crossing the Gen1 animals to a genetically distinguishable inbred strain.

In each instance, to facilitate mapping and cloning of a putative modifier, animals that contain a putative modifier are crossed to genetically distinguishable germplasm because mapping methods demand differences between the animals that contain putative modifiers and strains used for mapping. However, polymorphic differences in the genetic backgrounds of these strains can obscure the phenotype modification exerted by an induced enhancer or suppressor mutation. This problem can be overcome by creating an index strain that differs from the founder strain only at single nucleotide polymorphisms (SNPs) peppered about its genome. Briefly, an isogenic index strain is created by mutagenizing the index strain using a mutagen that induces single nucleotide changes, such as ENU. The SNP-marked index strain is created by systematic brother-sister mating, starting with a son and a daughter of the mutagenized animal who had been mated to the animal carrying the index mutation. The process of sequential brother-sister sibmating gradually eliminates detrimental and lethal mutations. To validate that the introduced SNP markers are phenotypically neutral, the index phenotype of the SNP-marked strain can be assessed. By way of example, ENU mutagenesis of BTBR or B6 mouse strains can be expected to produce such marker polymorphisms at a density in the range of 1 per centiMorgan. The approach of preparing such an index strain permits genetic screens to be as close to isogenic as one can envision.

The methods for identifying heterozygous carriers of enhancers and suppressors of an index phenotype can be effectively guided by applying an appropriate statistical analysis to the phenotypic data in candidate kindreds (e.g., tumor count, in the case of Min). Using the algorithm, it is possible to enhance the efficiency with which one identifies likely carriers and noncarriers of a candidate heterozygous modifier gene.

The first part of a suitable two-part statistical analysis, confirms the presence of a modifier gene segregating in a candidate kindred by applying a likelihood ratio test of the null hypothesis that no phenotype-modifying gene is segregating. The likelihood ratio test considers the alternative hypothesis that one modifier gene is segregating, and the test is calibrated exactly by Monte Carlo; that is, a p-value is obtained by calculating the likelihood ratio statistic repeatedly for random permutations of animals among subkindreds. For a discrete phenotype such as tumor count, background and modified phenotype distributions are modeled as negative binomials. Gaussian distributions may be appropriate for continuous phenotypes. If the p-value>0.05, there is no evidence for a modifier gene. Either more data are needed, or different kindreds should be considered for further analysis.

If the p-value<0.05, then, in the second part of the analysis, a LOD score for the presence of the modifier gene is calculated for each potential carrier that has offspring with phenotype information. The LOD score is the base 10 logarithm of the ratio of the probability of offspring phenotype data if the animal carries the modifier gene compared to the probability of the phenotype data if the animal does not carry the modifier gene. Probabilities are calculated from an estimated background distribution for the denominator, and from a mixture of the estimated background and estimated modified distribution for the numerator. Estimated distributions are obtained by the method of maximum likelihood. Negative binomial distributions can be used for tumor count phenotype, and Gaussian distributions can be used for continuous phenotypes. Potential carriers are then ranked according to their LOD scores. Mapping proceeds by first analyzing animals with highest positive LOD scores (likely carriers) and highest negative LOD scores (likely noncarriers).

An ENU-induced modifier mutation can be mapped to low resolution on the basis of their heterozygous phenotype, as outlined above. As detailed near the end of the Example below, higher resolution mapping is available when homozygotes for the ENU-induced modifier mutation have a qualitatively distinct phenotype such as lethality.

The invention will be better understood upon consideration of the following non-limiting Example.

EXAMPLE

The Min mutation, described by Moser et al., "A Dominant Mutation that Predisposes to Multiple Intestinal Neoplasia in the Mouse," *Science* 247:322–324 (1990), incorporated herein by reference, is a dominantly transmitted, fully penetrant mouse mutation that causes a phenotype in heterozygotes that closely resembles human inherited colonic polyposis syndromes. In this example, C57BL/6 mice carrying the Min allele were bred with genetically-distinguishable BTBR mice that carried random point mutations inherited from mutagenized fathers.

At approximately 1 month intervals, 6 to 12 male BTBR mice were treated with ENU according to the protocol described by Shedlovsky, supra, and were then crossed to female, unmutagenized BTBR mice. The Gen1 offspring of that cross were isogenic BTBR animals heterozygous for possible mutations that could affect the tumor load in mice that contain the Min mutation. Approximately 900 female Gen1 offspring were obtained over time.

Two hundred ninety-five Gen1 female mice were crossed with B6-Min male mice. As an aside, it is noted that multiple Gen1 males could have been crossed with B6-Min females, if the litters had been raised by foster mothers (such as ICR mice, commercially available) within a few days of birth. Over 90% of such pups survive. This strategy would be advantageous in that by providing multiple B6-Min females, production of a sufficient number of Gen1$F_1$ animals would be accelerated.

To perform the cross, two females and one male were placed in a cage. After two weeks, the females were withdrawn and replaced by two new females. Pregnancies were detected by weekly palpation of separated females. If no pregnancy was detected after two weeks of separation, the female was recycled into matings. The Gen1$F_1$ progeny from each female were genotyped for Min and were screened for signs of illness twice weekly starting at 100 days of age. When the animals began to look pale they were screened daily until they appeared close to death. The genotypic analysis employed allele-specific PCR or allele-specific hybridization, as described by Dietrich et al., supra, at page 637, and papers cited therein, all incorporated herein by reference, using the same PCR primers and conditions used by Dietrich et al.

Among the progeny were 92 kindreds having 6 or more members. Of these 92 kindreds, 5 kindreds showed at least two Min/+ members with possible enhancement of the Min phenotype (that is, a survival time shorter than the 90th percentile survival of the total population of Gen1F$_1$ mice). Seven kindreds showed at least two Min/+ members with suppression of the Min phenotype (that is, longer survival than the 10th percentile). As expected, the enhancement or suppression of the phenotype segregated within a kindred, since the Min mice in the Gen1F$_1$ generation of a kindred are heterozygous for any newly-induced mutations.

The following table shows survival of four kindreds that include segregating candidate enhancer or suppressor loci:

| Kindred Number | Mouse Number | Born | Died | Last Age | % survival on Gen1F$_1$ curve |
| --- | --- | --- | --- | --- | --- |
| Su248 | 1 | 10/20/yr1 | 11/11/yr2 | 388 | 2.9 |
| | 3 | 10/20/yr1 | 08/21/yr2 | 306 | 5.3 |
| | 2 | 10/20/yr1 | 07/26/yr2 | 280 | 6.6 |
| | 6 | 10/20/yr1 | 04/12/yr2 | 175 | 32.1 |
| Su258 | 4 | 10/11/yr1 | 11/12/yr2 | 398 | 0.0 |
| | 2 | 10/11/yr1 | 10/16/yr2 | 371 | 3.4 |
| | 14 | 02/14/yr2 | 09/30/yr2 | 229 | 11.0 |
| | 6 | 12/13/yr1 | 07/01/yr2 | 201 | 17.0 |
| | 7 | 12/13/yr1 | 06/19/yr2 | 189 | 22.4 |
| | 3 | 10/11/yr1 | 04/16/yr2 | 188 | 22.6 |
| | 11 | 12/13/yr1 | 05/25/yr2 | 164 | 43.3 |
| En333 | 15 | 03/06/yr2 | 08/05/yr2 | 152 | 56.1 |
| | 3 | 10/25/yr1 | 03/14/yr2 | 141 | 70.8 |
| | 12 | 03/06/yr2 | 07/23/yr2 | 139 | 72.7 |
| | 2 | 10/25/yr1 | 03/12/yr2 | 139 | 72.7 |
| | 13 | 03/06/yr2 | 06/18/yr2 | 104 | 98.7 |
| | 11 | 03/06/yr2 | 06/18/yr2 | 104 | 98.7 |
| | 10 | 03/06/yr2 | 06/18/yr2 | 104 | 98.7 |
| | 17 | 03/06/yr2 | 06/18/yr2 | 104 | 98.7 |
| En425 | 3 | 11/10/yr1 | 04/05/yr2 | 147 | 62.7 |
| | 1 | 11/10/yr1 | 03/25/yr2 | 136 | 76.4 |
| | 2 | 11/10/yr1 | 03/12/yr2 | 123 | 89.5 |
| | 6 | 11/10/yr1 | 03/12/yr2 | 123 | 89.5 |
| | 8 | 11/10/yr1 | 02/27/yr2 | 109 | 97.3 |
| | 6 | 11/10/yr1 | 02/27/yr2 | 109 | 97.3 |

If the probability is 10% that a mouse of normal genotype will survive longer than a particular age, the random probability that 2 mice in the same kindred will survive longer than that age is only 1%. The random probability that 3 mice in a kindred will survive longer is only 0.1%, in turn. Therefore, as the number of members of a kindred having an outlying short or long survival increases, so does the likelihood that the deviation results from a bona fide mutation inherited from the mutagenized BTBR founder animal. This is the cluster principle of the method. By predetermining a desired level of clustering, one can set limits on the ability to detect mutants and can raise the purification level of mutants obtained, thereby enriching the screen for mutants.

Figure 1:
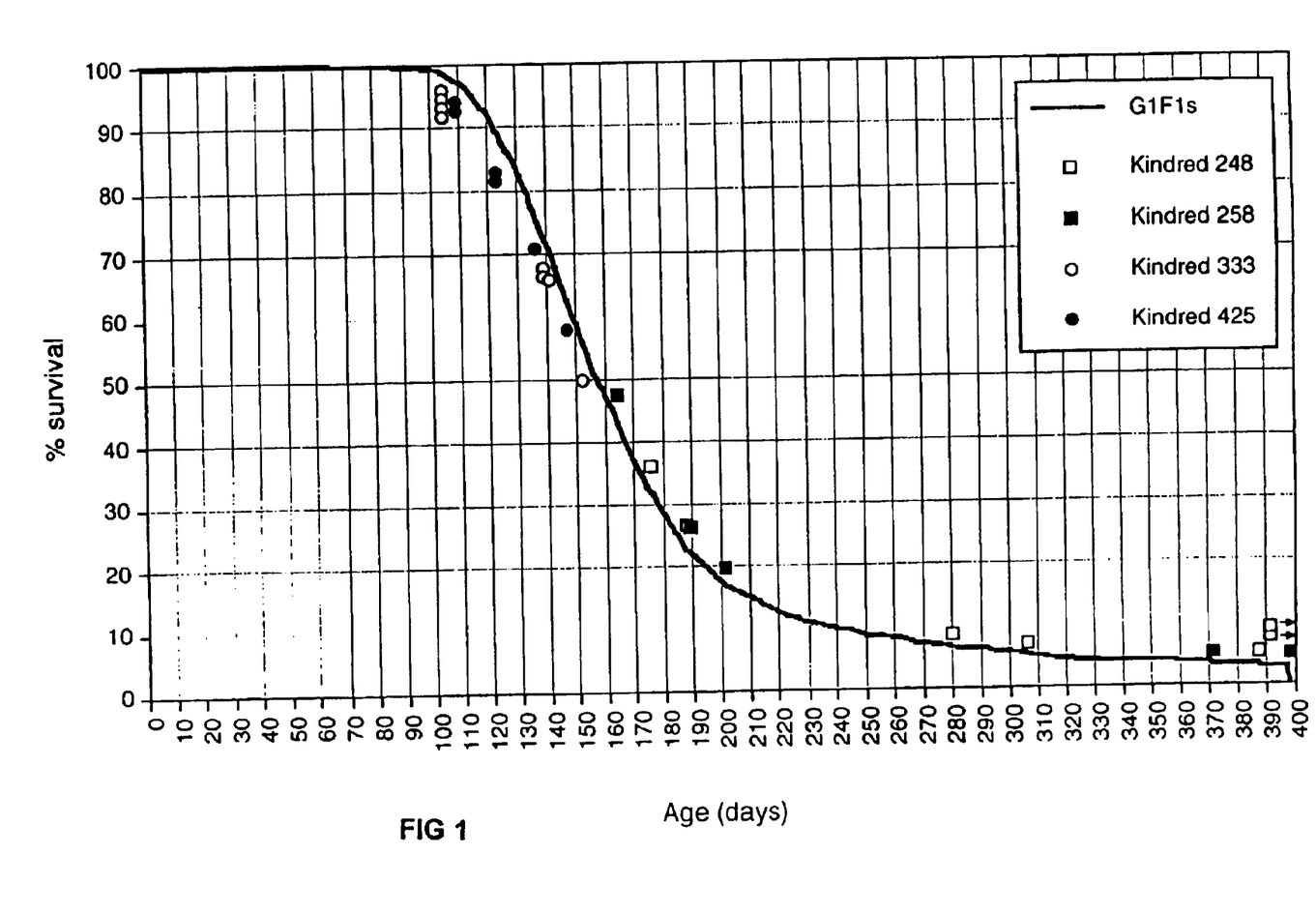
FIG. 1 depicts the probability of survival of Gen1F$_1$ mice bred in accordance with the method of the present invention.

FIG. 1 depicts the probability of survival versus age in the Gen1F$_1$ generation of the cross between Gen1 BTBR females and B6-Min males. The symbols below and to the left of the curve reflect individuals in 2 kindreds thought to contain mutations that enhance the Min phenotype (En333 and En425). The symbols above and to the right of the curve reflect the members of 2 kindreds for whom the Min phenotype appears to be suppressed (Su248 and Su258). A number of the mice in the latter category remained alive at more than 365 days of age. Mice that showed statistically lower or higher survival were bred using standard methods to maintain the mutation. In some cases, the Gen1 animal failed to breed and the long term surviving Gen1F$_1$ mice were bred to the wild-type founder strain instead, as a fallback method for rescuing mutations of interest. For example, the founder parent of kindred Su258, described infra, was not able breed after a candidate mutation was identified in her progeny. Long-lived progeny animals number 2 and 4 were, therefore, bred to BTBR mice.

To verify that these outlying members of a kindred do indeed contain an enhancing or suppressing mutation, a second-generation kindred was examined. This is useful both to recover carriers of a strong enhancer mutation and to detect more subtle dominant affects of either the suppressor or the enhancer class. Commonly, heterozygotes for a loss of gene function show only a subtle heterozygous effect.

To produce the second generation kindred, the founder animal that gave rise to a kindred that evidenced either an enhancing or suppressing function was crossed to normal BTBR animals. On average, 50% of the offspring of this cross would be expected to contain the suppressing or enhancing mutation. The offspring of this cross, termed Gen2, were crossed to B6-Min mice.

After 90 days, the progeny shown by genotypic analysis to carry the Min mutation were sacrificed and tumor load was assessed using standard methods for determining average tumor volume and number. Tumor load is defined as average tumor volume times the number of tumors per mouse.

As further proof that a suppressing mutation was obtained in kindred 258, two of the long-term survivors in the Gen1F$_1$ generation were bred and descendants were found to have very low tumor counts (about 10 or fewer tumors). This provided strong evidence that a bona fide mutation having the effect of suppressing the Min phenotype was segregating upon passage to the offspring. On the basis of 699 animals in suppressor kindred 258, the statistically estimated tumor multiplicity of +/+ animals is 18.8, on average, while that of the Su/+ animals is estimated as 5.8. For enhancer kindred 333, the estimated tumor multiplicity of the +/+ animals is 20.5 while the En/+ members of the kindred have an estimated tumor multiplicity of 36.

Because of the known SSLP polymorphisms between B6 and BTBR DNA, it will be possible to isolate the portion of the progeny genome that contains BTBR DNA and thereafter to localize the point mutation responsible for modifying the phenotype using standard techniques now available to the skilled molecular geneticist. The fact that ENU-induced mutations are single basepair substitutions makes this step particularly powerful. This is the basis for the "Modifying Molecule" appellation of the ICMM method. The portion of the genome containing the point mutation can be compared against known ESTs, or can be sequenced de novo to determine the genetic sequence responsible for encoding the molecule that modifies the phenotype. Using standard methods, the genetic sequence can be introduced into a suitable genetic construct containing a transcriptional promoter for production in a prokaryotic or eukaryotic host cell. One could use the cloned gene to produce other mutations in this gene in companion mouse strains.

The genetic sequence is readily compared against known sequences from humans to determine the identity of the corresponding human gene. The human gene can be isolated by standard methods of hybridization, PCR, or expression cloning. The human protein can likewise be obtained using standard techniques, either by isolation from human tissue, or by production in a non-native host using recombinant DNA methods.

It may be possible to isolate mutations that suppress the index Min phenotype in a more compact, albeit less sensitive, method. In this method, B6-Min (heterozygous) female mice are crossed directly with ENU-mutagenized BTBR male mice. As a control, non-mutagenized BTBR male mice are also processed in the same way. The $F_1$ offspring are fostered on ICR mice. Male $F_1$ mice that have the Min phenotype are maintained.

At 170 days, any $Apc^{Min/+}$ $F_1$ male whose body weight is greater than 95% of the control body weight is considered a candidate carrier of a dominant suppressor of the Min phenotype, Su/+.

Such candidate carriers are bred at 170 days of age to wild-type B6 female mice. The female offspring of this cross ($Apc^{min/+}$ and $Apc^{+/+}$) are backcrossed to the candidate male who is by now only about 230 days old.

The progeny of the latter cross are then phenotyped at 90 days of age. By this time, the candidate male is at least 340 days old. Among the progeny, any detrimental or lethal phenotypes will inform about the map position of the suppressor and will indicate whether the candidate male carries a suppressor mutation.

| $Apc^{Min/+}$ | Progeny: |
|---|---|
| +/+ | normal Min phenotype |
| Su/+ | low tumor load at 90 days? |
| Su/Su | very low tumor load at 90 days? or detrimental or lethal? |

| $Apc^{+/+}$ | Progeny: |
|---|---|
| +/+ | normal |
| Su/+ | normal? |
| Su/Su | detrimental or lethal? |

Detrimentally affected animals will be homozygous for BTBR markers linked to the suppressor locus. By contrast, if Su/Su is an embryonic lethal mutation, the set of liveborn progeny will lack animals homozygous for BTBR markers linked to the suppressor locus.

It may also be important to rescue germplasm carrying a modifier mutation that enhances or suppresses, but particularly those that enhance, the Min phenotype, using in vitro fertilization. For example, a candidate carrier male who might be too sick to breed can be sacrificed. Sperm taken from the sacrificed male can be used to fertilize eggs obtained from a suitable female (e.g., BTBR or a mouse that carries the mutation of interest). The techniques that can be employed are described in Hogan, B. et al., *Manipulation of the Mouse Embryo,* Cold Spring Harbor Laboratory Press, 2nd. ed. (1994), incorporated herein by reference.

It is intended that the foregoing examples are non-limiting on the invention, but rather that the invention encompasses all such modifications and variations as come within the scope of the following claims.

We claim:

1. A method for identifying a segregating single point mutation at a genetic locus that modifies an index phenotype in a non-human index inbred strain, the segregating mutation causing an outlying phenotype relative to the index phenotype, the method comprising the steps of:

outcrossing at least one male animal of a non-human founder inbred strain to at least one female animal of a non-human index inbred strain to obtain F1 progeny, the founder inbred strain carrying random point mutations relative to a wild-type animal of the founder inbred strain, the index inbred strain carrying a congenic dominant allele at a locus known to confer the index phenotype and being genetically distinguishable from the founder inbred strain, identifying one or more $F_1$ individuals displaying an outlying phenotype relative to the index phenotype displayed by the index inbred strain, thereby indicating that at least one $F_1$ individual possesses an index phenotype-modifying mutation;

backcrossing gametes from male F1 progeny to at least one female of the index inbred strain, with or without the index allele, to obtain N2 backcross progeny, wherein at least one of the N2 backcross progeny that carry the dominant allele also exhibit the outlying phenotype; and verifying that the outlying phenotype is caused by a segregating single point mutation.

2. A method as claimed in claim 1 wherein any of the crosses employ preserved gametes.

3. A method as claimed in claim 1 wherein the segregating mutation is a heterozygous modifier of the index phenotype selected from a group consisting of an enhancing modifier and a suppressing modifier.

4. A method as claimed in claim 1 wherein the dominant allele is a Min allele at an Apc locus in a mouse.

5. A method as claimed in claim 1 wherein the index inbred strain and the founder inbred strain share an isogenic genetic background.

6. A method as claimed in claims further comprising the step of mapping the segregating mutation using a mapping partner strain, the mapping partner strain being produced by the steps of:

treating an animal of the founder strain with a mutagenic agent to induce point mutations in the treated animal, crossing the treated animal to an animal of the founder strain to produce $F_1$ progeny; and sib-mating $F_1$ and subsequent generation progeny until detrimental and lethal mutations are eliminated.

7. A method as claimed in claim 5 wherein the method identifies a segregating mutation at a genetic locus that modifies tumor multiplicity in a C57BL/6 mouse congenic for the Min allele at the Apc locus, the method comprising the steps of:

outcrossing at least one male C57BL/6 mouse carrying random point mutations to a female C57BL/6 mouse congenic for the Min allele at the Apc locus to obtain F1 progeny;

identifying one or more $F_1$ individuals displaying an outlying tumor multiplicity phenotype relative to the tumor multiplicity phenotype in a C57BL/6 mouse congenic for the Min allele at the Apc locus, thereby indicating that at least one $F_1$ individual possesses a segregating mutation that modifies tumor multiplicity; and backcrossing gametes from male F1 progeny to at least one female C57BL/6 mouse congenic for the Min allele at the Apc locus to obtain N2 backcross progeny, wherein at least one of the N2 backcross progeny carries the Min allele and has a tumor multiplicity that is modified relative to tumor multiplicity in a C57BLJ6 mouse congenic for the Min allele at the Apc locus, the modified tumor multiplicity being characteristic of the segregating mutation thereby identified.

8. A method as claimed in claim 7 the modified tumor multiplicity is evaluated according to a method comprising the steps of:

repeatedly applying for random permutations of mice among N2 backcross subkindreds a likelihood ratio test of the null hypothesis that no multiplicity modifier is segregating to obtain a p-value, wherein a p-value of less than 0.05 indicates a potential carrier of the segregating mutation;

when the p-value is less than 0.05, calculating, for each potential carrier that has offspring with information about tumor multiplicity, a LOD score for presence of the segregating mutation, wherein the LOD score is $\log_{10}$ of a ratio of a first probability of offspring phenotype data if the potential carrier mouse carries a multiplicity modifier to a second probability of offspring phenotype data if the potential carrier mouse does not carry a multiplicity modifier, and wherein the second probabilities are calculated from an estimated background distribution and the first probabilities are calculated from a mixture of the estimated background distribution and an estimated modified distribution, where the estimated distributions are obtained by a maximum likelihood method, and ranking the LOD scores of potential carriers, whereby animals having the highest LOD scores are likely carriers of the segregating mutation.

9. A method as claimed in claim 7, further comprising the step of mapping the segregating mutation in the N2 backcross progeny using a mapping partner strain having a C57BL/6 genetic background.

10. A method as claimed in claim 9 wherein the mapping partner strain is produced by the steps of:

treating a C57BL/6 mouse with a mutagen to introduce random point mutations; crossing the treated mouse to a C57BL/6 mouse to produce F1 progeny; and sib-mating F1 and subsequent generation progeny until detrimental and lethal mutations are eliminated.

11. A method as claimed in claim 1 wherein the founder inbred mouse strain is produced by a method comprising the step of treating a wild-type inbred mouse with a mutagenic agent to induce point mutations.

12. A method as claimed in claim 11 wherein the mutagenic agent is ethylnitrosourea.

13. A method for identifying a human genetic sequence that corresponds to a segregating mutation at a genetic locus in a non-human animal, the segregating mutation causing an outlying phenotype relative to an index phenotype in an index inbred mouse strain, the method comprising the steps of:

outcrossing a founder inbred non-human strain to an index inbred non-human strain to obtain $F_1$ progeny, the founder inbred strain carrying random point mutations relative to a wild-type animal of the founder inbred strain, the index inbred strain carrying a dominant allele at a locus known to confer the index phenotype and being genetically distinguishable from the founder inbred strain, wherein some of the $F_1$ progeny that carry the dominant allele also carry at least one random mutation;

backcrossing the $F_1$ progeny to the index inbred strain, with or without the index allele, to obtain N2 backcross progeny, wherein at least some of the N2 backcross progeny that carry the dominant allele also exhibit the outlying phenotype;

verifying that the outlying phenotype is caused by a segregating mutation;

identifying genetic markers linked to the segregating mutation;

identifying a gene on a contig that encodes the segregating mutation; and recovering human genetic sequences that correspond to the mutation-encoding gene.

14. A method for identifying a segregating mutation at a genetic locus that modifies an index phenotype in a non-human index inbred strain, the segregating mutation causing an outlying phenotype relative to the index phenotype, the method comprising the steps of:

crossing a non-human founder inbred strain with a non-human index inbred strain to obtain Gen1 progeny, the founder inbred strain carrying random point mutations relative to a wild-type animal of the founder inbred strain, the index inbred strain carrying a congenic dominant allele at a locus known to confer the index phenotype, the founder strain and the index strain sharing an isogenic genetic background, wherein some of the Gen1 progeny that carry the dominant allele also exhibit a modified index phenotype; and verifying that Gen1 progeny that carry the dominant allele and exhibit a modified index phenotype carry a segregating mutation.

15. A method as claimed in claim 14 wherein the genetic background has no modifying effect upon the index phenotype.

16. A method as claimed in claim 14 the genetic background has a modifying effect upon the index phenotype.

17. A method as claimed in claim 16 wherein the genetic background has an enhancing effect upon the index phenotype, and wherein the Gen1 animals exhibit a suppressed phenotype relative to the index inbred strain.

18. A method as claimed in claim 4 further comprising the steps of:

mapping the segregating mutation by crossing Gen1 animals that have the dominant allele and a modified index phenotype to a genetically distinguishable inbred strain; and evaluating the progeny of the mapping cross.

19. A method as claimed an claim 18 wherein the genetically distinguishable inbred strain shares an isogenic genetic background with the founder and index strains and further comprises single nucleotide polymorphisms relative to the founder inbred strain.

20. A method for identifying a segregating mutation at a genetic locus that modifies an index phenotype in a non-human index inbred strain, the segregating mutation causing an outlying phenotype relative to the index phenotype, the method comprising the steps of:

outcrossing a non-human founder inbred strain with the non-human index inbred strain to obtain Gen1$F_1$ progeny, the founder strain being heterozygous only for random point mutations relative to a wild-type animal of the founder inbred strain, the index inbred strain carrying a dominant allele at a locus known to confer the index phenotype, where at least some of the Gen1$F_1$ progeny carry both the dominant allele and at least one random mutation;

crossing a founder animal of the founder inbred strain to an animal of the founder strain that lacks the mutations to obtain Gen2 offspring, where the founder animal has at least one outcrossed $F_1$ progeny that displays the outlying phenotype relative to the index phenotype, outcrossing Gen2 offspring to the index strain to obtain Gen2$F_1$ backcross progeny, half of which, on average, carry the dominant allele that confers the index phenotype; and verifying that a subset of the Gen2$F_1$ progeny shows the outlying phenotype.

21. A method for identifying a segregating single point mutation at a genetic locus that modifies an index phenotype in a mouse index inbred strain, the segregating mutation causing an outlying phenotype relative to the index phenotype, the method comprising the steps of:

outcrossing at least one male animal of a mouse founder inbred strain to at least one female animal of a mouse index inbred strain to obtain F1 progeny, the founder inbred strain carrying random point mutations relative to a wild-type animal of the founder inbred strain, the index inbred strain carrying a congenic dominant allele at a locus known to confer the index phenotype and being genetically distinguishable from the founder inbred strain, identifying one or more $F_1$ individuals displaying an outlying phenotype relative to the index phenotype displayed by the index inbred strain, thereby indicating that at least one $F_1$ individual possesses an index phenotype-modifying mutation;

backcrossing gametes from male F1 progeny to at least one female of the index inbred strain, with or without the index allele, to obtain N2 backcross progeny, wherein at least one of the N2 backcross progeny that carry the dominant allele also exhibit the outlying phenotype, and verifying that the outlying phenotype is caused by a segregating single point mutation.

22. A method as claimed in claim 21 wherein any of the crosses employ preserved gametes.

23. A method as claimed in claim 21 wherein the dominant allele is a Min allele at an Apc locus in a mouse.

24. A method as claimed in claim 21 wherein the index inbred strain and the founder inbred strain share an isogenic genetic background.

25. A method as claimed in claim 24 further comprising the step of mapping the segregating mutation using a mapping partner strain produced by the steps of:

treating an animal of the founder strain with a mutagenic agent to induce point mutations in the treated animal;

crossing the treated animal to an animal of the founder strain to produce $F_1$ progeny; and sib-mating $F_1$ and subsequent generation progeny until detrimental and lethal mutations are eliminated.

26. A method as claimed in claim 24 wherein the method identities a segregating mutation at a genetic locus that modifies tumor multiplicity in a C57BL/6 mouse congenic for the Min allele at the Apc locus, the method comprising the steps of:

outcrossing at least one male C57BL/6 mouse carrying random point mutations to a female C57BL/6 mouse congenic for the Min allele at the Apc locus to obtain F1 progeny, wherein at least one of the F1 progeny carries both the Min allele and a random point mutation; and backcrossing gametes from male F1 progeny to at least one female C57BL/6 mouse congenic for the Min allele at the Apc locus to obtain N2 backcross progeny, wherein at least one of the N2 backcross progeny carries the Min allele and has a tumor multiplicity that is modified relative to tumor multiplicity in a C57BL/6 mouse congenic for the Min allele at the Ape locus, the modified tumor multiplicity being characteristic of the segregating mutation.

27. A method as claimed in claim 26 wherein the modified tumor multiplicity is evaluated according to a method comprising the steps of:

repeatedly applying for random permutations of mice among N2 backcross subkindreds a likelihood ratio test of the null hypothesis that no multiplicity modifier is segregating to obtain a p-value, wherein a p-value of less than 0.05 indicates a potential carrier of the segregating mutation;

when the p-value is less than 0.05, calculating, for each potential carrier that has offspring with information about tumor multiplicity, a LOD score for presence of the segregating mutation, wherein the LOD score is $\log_{10}$ of a ratio of a first probability of offspring phenotype data if the potential carrier mouse carries a multiplicity modifier to a second probability of offspring phenotype data if the potential carrier mouse does not carry a multiplicity modifier, and wherein the second probabilities are calculated from an estimated background distribution and the first probabilities are calculated from a mixture of the estimated background distribution and an estimated modified distribution, where the estimated distributions are obtained by a maximum likelihood method; and ranking the LOD scores of the potential carriers, whereby animals having the highest LOD scores are likely carriers of the segregating mutation.

28. A method as claimed in claim 26, further comprising the step of mapping the segregating mutation in the N2 backcross progeny using a mapping partner strain.

29. A method as claimed in claim 28 wherein the mapping partner strain is produced by the steps of:

treating a C57BL/6 mouse with a mutagen to introduce random point mutations;

crossing the treated mouse to a C57BL/6 mouse to produce F1 progeny; and sib-mating F1 and subsequent generation progeny until detrimental and lethal mutations are eliminated.

30. A method as claimed in claim 21 wherein the founder inbred mouse strain is produced by a method comprising the step of treating a wild-type inbred mouse with a mutagenic agent to induce point mutations.

31. A method as claimed in claim 30 wherein the mutagenic agent is ethylnitrosourea.

* * * * *